United States Patent
Kaneko et al.

(10) Patent No.: US 7,531,610 B2
(45) Date of Patent: May 12, 2009

(54) FLUOROSULFONYL GROUP-CONTAINING COMPOUND, METHOD FOR ITS PRODUCTION AND POLYMER THEREOF

(75) Inventors: Isamu Kaneko, Chiyoda-ku (JP);
Atsushi Watakabe, Chiyoda-ku (JP);
Jyunichi Tayanagi, Chiyoda-ku (JP);
Susumu Saito, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/010,586

(22) Filed: Jan. 28, 2008

(65) Prior Publication Data
US 2008/0146841 A1   Jun. 19, 2008

Related U.S. Application Data

(63) Continuation of application No. PCT/JP2006/314812, filed on Jul. 26, 2006.

(51) Int. Cl.
*C08F 16/24* (2006.01)
*C07C 309/00* (2006.01)

(52) U.S. Cl. .............. 526/243; 526/247; 526/250; 526/255; 526/286; 526/287; 562/825; 562/827; 562/828; 562/833

(58) Field of Classification Search ........... 526/243; 562/825, 827, 828, 833
See application file for complete search history.

(56) References Cited

U.S. PATENT DOCUMENTS

| 4,273,729 A | 6/1981 | Krespan |
| 2006/0106252 A1 | 5/2006 | Murata et al. |
| 2008/0146841 A1 | 6/2008 | Kaneko et al. |

FOREIGN PATENT DOCUMENTS

| EP | 1 596 453 A1 | 11/2005 |
| JP | 2004/143055 | 5/2004 |
| WO | WO 03/106515 A1 | 12/2003 |

(Continued)

OTHER PUBLICATIONS

STN search for U.S. Appl. No. 12/010,586, conducted on Nov. 20, 2008.*

(Continued)

*Primary Examiner*—Marc S. Zimmer
*Assistant Examiner*—Nicole M Buie
(74) *Attorney, Agent, or Firm*—Oblon, Spivak, McClelland, Maier & Neustadt, P.C.

(57) ABSTRACT

A compound containing two fluorosulfonyl groups which are groups convertible to sulfonic acid groups, an intermediate therefor, and methods for their production with high productivity, are provided. Also provided are a fluorosulfonyl group-containing polymer obtained by polymerizing such a compound, and a sulfonic acid group-containing polymer obtained from such a polymer.

A method for producing a compound of the following formula (m0), such a compound, a fluorosulfonyl group-containing polymer obtained by polymerizing such a compound, and a sulfonic acid group-containing polymer obtained from such a polymer, provided that $R^{F01}$ is a single bond or a $C_{1-6}$ bivalent perfluoro organic group, $R^{F02}$ is a $C_{1-6}$ bivalent perfluoro organic group, and n is 0 or 1:

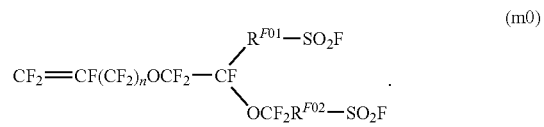

(m0)

14 Claims, 1 Drawing Sheet

FOREIGN PATENT DOCUMENTS

WO  WO 2004/066426 A1  8/2004
WO  WO 2005/003062 A2  1/2005

OTHER PUBLICATIONS

U.S. Appl. No. 12/019,355, filed Jan. 24, 2008, Shimohira, et al.
U.S. Appl. No. 12/021,842, filed Jan. 29, 2008, Yamada, et al.
U.S. Appl. No. 12/010,586, filed Jan. 28, 2008, Kaneko, et al.
U.S. Appl. No. 11/771,332, filed Jun. 29, 2007, Shimohira, et al.
U.S. Appl. No. 11/771,414, filed Jun. 29, 2007, Shimohira, et al.
U.S. Appl. No. 12/186,947, filed Aug. 6, 2008, Watakabe, et al.

\* cited by examiner

FLUOROSULFONYL GROUP-CONTAINING COMPOUND, METHOD FOR ITS PRODUCTION AND POLYMER THEREOF

TECHNICAL FIELD

The present invention relates to a compound containing two fluorosulfonyl groups, an intermediate thereof, methods for their production, a fluorosulfonyl group-containing polymer obtained by polymerizing such a compound, and a sulfonic acid group-containing polymer obtained from such a polymer.

BACKGROUND ART

Heretofore, a polymer having fluorosulfonyl groups ($-SO_2F$) in a copolymer of a fluorinated monomer of the following formula with tetrafluoroethylene, converted to sulfonic acid groups ($-SO_3H$), has been commonly used as an electrolyte material constituting an ion change membrane (such as a membrane to be used for electrolysis of sodium chloride or for a polymer electrolyte fuel cell) or a catalyst layer for a fuel cell. In the formula, Y represents a fluorine atom or a trifluoromethyl group, n is an integer of from 1 to 12, m is an integer of from 0 to 3, and p is 0 or 1, provided that m+p>0.

$$CF_2=CF-(OCF_2CFY)_m-O_p-(CF_2)_n-SO_2F$$

A sulfonic acid group-containing polymer (hereinafter referred to also as a sulfonic acid polymer) is a polymer which is capable of reducing the electric power for electrolysis when used in e.g. an electrolytic cell for sodium chloride in the form of a membrane having a high ion exchange capacity. Further, in a case where such a sulfonic acid polymer is used for a fuel cell, it is a polymer capable of improving the power generation energy efficiency. As such a sulfonic acid polymer, preferred is a polymer having a larger ion exchange capacity and a lower electric resistance.

A conventional fluorosulfonyl group-containing monomer is required to be copolymerized with tetrafluoroethylene having a high polymerization reactivity in order to obtain a perfluoropolymer having a high molecular weight. However, if it is attempted to increase the ratio of the fluorosulfonyl group-containing monomer to be used for copolymerization for the purpose of increasing the ion exchange capacity of the sulfonic acid polymer, there has been a problem that the molecular weight of the copolymer tends to be low. A membrane formed of a copolymer having a low molecular weight has had a problem that the mechanical strength and durability are inadequate, and as such, is not practically useful.

Under the circumstances, in order to maintain a high ion exchange capacity and to obtain a membrane having a high tetrafluoroethylene content to secure the strength, it has been proposed to use a monomer having two sulfonic acid groups or precursor groups capable of being converted to sulfonic acid groups, such as fluorosulfonyl groups, in its molecule. Namely, the following monomer is proposed in Patent Document 1:

$$[FSO_2(CF_2)_a][FSO_2(CF_2)_b]CF-Q^F-CF_2OCF=CF_2$$

In the above formula, a is an integer of from 1 to 3, b is an integer of from 1 to 3, and $Q^F$ is a single bond or a $C_{1-6}$ perfluoroalkylene group which may have an etheric oxygen atom.

To produce such a monomer, it is necessary to substitute fluorine atoms for all hydrogen atoms in an intermediate containing a structure of $[FSO_2(CH_2)_a][FSO_2(CH_2)_b]CH-$ by using fluorine gas, but such a process has had a problem that during the fluorination reaction, C—S bonds are likely to be broken, and the yield of fluorination is low. Further, there is no disclosure about a polymer obtained by polymerizing this monomer.

The following monomer is proposed in Patent Document 2.

$$(XSO_2)_kCY_1(CF_2)_mO(CFZCF_2O)_nCF=CF_2$$

In the above formula, k=2 or 3, k+1=3, m=0 to 5, n=0 to 5, X=F, Cl, OH, $O(M)_{1/L}$ (wherein M is a monovalent to trivalent metal, and L is the valence of the metal), OR (wherein R is a $C_{1-5}$ alkyl group, and such an alkyl group may be one containing an element other than carbon or hydrogen), or $A\text{-}(SO_2Rf)_aB$ (wherein A is nitrogen or carbon, as to a, a=1 when A is nitrogen and a=2 when A is carbon, B is hydrogen or a monovalent metal, and Rf is a perfluorinated alkyl group), Y=F, Cl or $CF_3$, and Z=F, Cl, $CF_3$, Br or I.

A sulfonic acid polymer obtainable from such a monomer has a structure wherein a plurality of sulfonic acid groups are bonded to one carbon atom, and there is concern about stability, as there is no information as to whether or not such a structure may have durability over a long period of time.

Patent Document 1: WO2005/003062 (claim 17)
Patent Document 2: WO03/106515 (claim 1)

DISCLOSURE OF THE INVENTION

Objects to be Accomplished by the Invention

It is an object of the present invention to provide a compound containing two fluorosulfonyl groups which are groups convertible to sulfonic acid groups, its intermediate, and methods for producing them with high productivity. Further, it is another object of the present invention to provide a fluorosulfonyl group-containing polymer obtained by polymerizing such a compound, and a sulfonic acid group-containing polymer obtained from such a polymer.

Means to Accomplish the Objects

The present invention provides the following:

(1) A method for producing a compound of the following formula (c), characterized in that a compound of the following formula (a) is reacted with a compound of the following formula (b1) or a compound of the following formula (b2) in the presence of $M^aF$ (wherein $M^a$ represents a metal atom capable of forming a monovalent cation) to obtain the compound of the following formula (c):

provided that the symbols in the formulae have the following meanings:

$R^{F01}$ is a single bond or a $C_{1-6}$ bivalent perfluoro organic group, and $R^{F02}$ is a $C_{1-6}$ bivalent perfluoro organic group.

(2) A process for producing a compound of the following formula (m0), characterized in that via a step of obtaining a compound of the following formula (c) by the method as defined in (1), a compound of the following formula (m0) is obtained:

(c)

(m0)

provided that the symbols in the formulae have the following meanings:

$R^{F01}$ is a single bond or a $C_{1-6}$ bivalent perfluoro organic group,

$R^{F02}$ is a $C_{1-6}$ bivalent perfluoro organic group, and n is 0 or 1.

(3) The process according to (2), wherein a compound of the following formula (c) is obtained by the method as defined in (1), then this compound is reacted with hexafluoropropene oxide in the presence of $M^aF$ (wherein $M^a$ represents a metal atom capable of forming a monovalent cation) to obtain a compound of the following is formula (d), and then, the compound is pyrolyzed to obtain a compound of the following formula $(m0_0)$:

(c)

(d)

$(m0_0)$ provided that in the formulae, $R^{F01}$ and $R^{F02}$ are as defined above.

(4) The process according to (2), wherein a compound of the following formula (c) is obtained by the method as defined in (1), then this compound is reacted with a compound of the following formula (e) in the presence of $M^bF$ (wherein $M^b$ represents an alkali metal atom) to obtain a compound of the following formula $(m0_1)$:

(c)

$CF_2$═$CFCF_2X$ (e)

$(m0_1)$ provided that the symbols in the formulae have the following meanings:

$R^{F01}$ and $R^{F02}$ are as defined above, and

X is —$OSO_2F$, —I, —Cl or —Br.

(5) The process according to (2), wherein the compound of the above formula (m0) is a compound of the following formula (m1):

(m1)

provided that the symbols in the formula have the following meanings:

$R^{F11}$ is a single bond or a $C_{1-6}$ linear perfluoroalkylene group which may have an etheric oxygen atom, $R^{F12}$ is a $C_{1-6}$ linear perfluoroalkylene group, and n is 0 or 1.

(6) A method for producing a polymer, characterized in that a compound of the following formula (m0) is polymerized to obtain a polymer comprising units based on the compound of the following formula (m0):

(m0)

provided that the symbols in the formula have the following meanings:

$R^{F01}$ is a single bond or a $C_{1-6}$ bivalent perfluoro organic group, $R^{F02}$ is a $C_{1-6}$ bivalent perfluoro organic group, and n is 0 or 1.

(7) A method for producing a polymer, characterized in that a compound of the following formula (m0) and tetrafluoroethylene are copolymerized to obtain a polymer comprising units based on the compound of the following formula (m0) and units based on tetrafluoroethylene:

(m0)

provided that the symbols in the formula have the following meanings:
$R^{F01}$ is a single bond or a $C_{1-6}$ bivalent perfluoro organic group,
$R^{F02}$ is a $C_{1-6}$ bivalent perfluoro organic group, and
n is 0 or 1.

(8) A compound of the following formula (m1):

(m1)

provided that the symbols in the formula have the following meanings:
$R^{F11}$ is a single bond or a $C_{1-6}$ linear perfluoroalkylene group which may have an etheric oxygen atom,
$R^{F12}$ is a $C_{1-6}$ linear perfluoroalkylene group, and
n is 0 or 1.

(9) A compound of the following formula (m11):

(m11)

(10) A compound of the following formula (m12):

(m12)

(11) A compound of the following formula (m13):

(m13)

(12) A polymer comprising units based on the compound as defined in any one of (8) to (11).

(13) A polymer comprising units based on the compound as defined in any one of (8) to (11) and units based on tetrafluoroethylene.

(14) A polymer having the —SO$_2$F groups of the polymer as defined in (12) or (13) converted to —SO$_3$H groups.

(15) A compound of the following formula (c1):

(c1)

(16) A compound of the following formula (c2):

(c2)

(17) A compound of the following formula (d1):

(d1)

(18) A compound of the following formula (d2):

(d2)

Effects of the Invention

According to the present invention, it is possible to provide a compound containing two fluorosulfonyl groups which are groups convertible to sulfonic acid groups, a compound very useful as a reaction intermediate for such a compound, and a polymer obtainable by polymerizing such a compound, which has two sulfonic acid groups in one side chain. The polymer of the present invention has a higher softening temperature, and is superior in mechanical strength as compared with a polymer which has one sulfonic acid group in one side chain. Further, a polymer electrolyte made of the polymer of the present invention has a low resistance. Further, the compound and the polymer of the present invention are easy to produce, and their industrial applications are easy.

BEST MODE FOR CARRYING OUT THE INVENTION

In this specification, the compound of the formula (m0) will be represented by the compound (m0). The units based on the compound of the formula (m0) contained in a polymer will be represented by the units (m0). The polymer containing the units (m0) will be represented by the polymer (m0). The compounds, units, and polymers represented by other formulae will be represented in the same manner.

Units in a polymer are meant for monomer units (referred to also as repeating units) derived from a monomer, which are formed by polymerization of such a monomer. However, units in the present invention may be units formed directly by a polymerization reaction or units formed by chemical modification after the polymerization reaction.

In this specification, an organic group is meant for a group containing at least one carbon atom.

By the process of the present invention, the compound (m0) is obtainable (where $R^{F01}$, $R^{F02}$ and n are as defined above, the same applies hereinafter). Here, $R^{F01}$ being a single bond means that the $SO_2F$ group is bonded directly to the carbon atom of the CF group (the same applies hereinafter).

(m0)

The compound (m0) is preferably represented as the compound (m1) (where $R^{F11}$ and $R^{F12}$ are as defined above, the same applies hereinafter).

(m1)

$R^{F11}$ is more preferably a $C_{1-6}$ linear perfluoroalkylene group which may have an etheric oxygen atom, particularly preferably a $C_{1-6}$ linear perfluoroalkylene group which may have an etheric oxygen atom between carbon atoms of a carbon atom-carbon atom bond. From the viewpoint of availability of the starting materials and purification by distillation of the monomer, it is further preferably a $C_{1-4}$ linear perfluoroalkylene group which may have an etheric oxygen atom between carbon atoms of a carbon atom-carbon atom bond. If the carbon number is too large, the boiling point tends to be high, and purification by distillation tends to be difficult.

$R^{F12}$ is more preferably a $C_{1-4}$ linear perfluoroalkylene group.

From the viewpoint of availability of starting materials, the yield, and purification by distillation, preferred specific examples of the compound (m0) are the following compounds (m11), (m12) and (m13).

(m11)

(m12)

(m13)

In the present invention, the compound $(m0_0)$ (the compound (m0) wherein n=0) may be prepared by the following procedure.

(1) A perfluorocompound (a) containing a fluorosulfonyl group is reacted with a compound (b1) or a compound (b2) in the presence of $M^aF$ (where $M^a$ is a metal atom capable of forming a monovalent cation) to obtain a compound (c).

(2) The compound (c) is reacted with hexafluoropropene oxide in the presence of $M^aF$ (where $M^a$ is as defined above) to obtain a compound (d).

(3) The compound (d) is directly pyrolyzed, or after once converting the —COF group to a —COOM$^C$ group (where $M^C$ is an alkali metal atom), pyrolyzed, to convert it to a compound $(m0_0)$.

(a)

(b1)

(b2)

(c)

(d)

$(m0_0)$

As the starting material compound (a) in the above reaction (1), the following compounds may preferably be used.

(a1)

(a2)

The compound (a1) may be prepared by oxidizing $CF_2$=$CFCF_2CF_2SO_2F$ with hydrogen peroxide, NaClO or oxygen. In a case where oxygen gas is used, the oxidation reaction may be carried out in the presence of an inert solvent (such as fluorotrichloromethane, trichlorotrifluoroethane, pentafluorodichloropropane or perfluorocyclobutane), or may be carried out in the absence of a solvent. The temperature for the reaction is preferably from 50° C. to 200° C., more preferably from 80° C. to 150° C., from the viewpoint of the yield and the reaction selectivity.

Likewise, the compound (a2) may be prepared by oxidizing $CF_2$=$CFCF_2OCF_2CF_2SO_2F$ with oxygen. A preparation example of the compound (a2) is disclosed in JP-A-57-176973. $CF_2$=$CFCF_2OCF_2CF_2SO_2F$ used here may be prepared from $FOCCF_2SO_2F$, KF and $CF_2$=$CFCF_2OSO_2F$ (U.S. Pat. No. 4,273,729, etc.). And, $FOCCF_2SO_2F$ may be prepared by isomerizing tetrafluoroethane-β-sultone (aftermentioned compound (b11)) by reacting it with an amine such as triethylamine or a basic catalyst such as KF or NaF (Journal of American Chemical Society, vol. 82, pp. 6181-6199, (1960), Inorganic Chemistry Vol. 30, pp. 4821-4826, (1991), WO2003/106409). Namely, $CF_2$=$CFCF_2OCF_2CF_2SO_2F$ has heretofore been prepared by two stage reactions via $FOCCF_2SO_2F$ from tetrafluoroethane-β-sultone as the starting material.

However, in reality, it can be prepared by reacting tetrafluoroethane-β-sultone, KF and $CF_2$=$CFCF_2OSO_2F$ without isolating $FOCCF_2SO_2F$ as the intermediate. Specifically, for example, in the presence of a solvent such as tetraglyme, KF and tetrafluoroethane-β-sultone are reacted under cooling, and $CF_2$=$CFCF_2OSO_2F$ is dropwise added thereto and reacted, whereby $CF_2$=$CFCF_2OCF_2CF_2SO_2F$ can be obtained.

As the compound (b1), the following compounds may, for example, be mentioned.

(b11)

(b12)

(b13)

(b14)

As the compound (b2), the following compounds may, for example, be mentioned.

$FSO_2$—$CF_2$—$COF$  (b21)

$FSO_2$—$CF(CF_3)$—$COF$  (b22)

$FSO_2$—$CF_2CF_2$—$COF$  (b23)

$FSO_2$—$CF_2CF_2CF_2$—$COF$  (b24)

In the above reaction (1), it is preferred to use an aprotic polar solvent. As such a solvent, monoglyme, diglyme, triglyme, tetraglyme, acetonitrile, propionitrile, adiponitrile, benzonitrile, dioxane, tetrahydrofuran, dimethylformamide, dimethyl sulfoxide, N-methylpyrrolidone or nitroethane may, for example, be mentioned. A mixed solvent of these may also be used. The reaction temperature is preferably from −80° C. to +200° C., more preferably from −30° C. to +50° C.

$M^aF$ may, for example, be potassium fluoride, cesium fluoride, silver fluoride or quaternary ammonium fluoride. Cesium fluoride and potassium fluoride are particularly preferred.

Each of the compound (b1) and the compound (b2) will react with $M^aF$ to form $M^aOCF_2R^{F02}$—$SO_2F$, which is reacted with the compound (a) to form the compound (c). The compound (b1) may be isomerized to the compound (b2) in the presence of a base such as potassium fluoride or triethylamine, and then used.

The above reaction (2) is, like the reaction (1), a reaction of a compound (c) having a fluoroformyl group with hexafluoropropene oxide as an epoxy compound and may be carried out under a reaction condition similar to the reaction (1). In a case where a 2 mol adduct of hexafluoropropene oxide is formed, it is possible to improve the yield by decreasing the amount of hexafluoropropene oxide to control the conversion to be low and recovering an unreacted compound (c) from the reaction mixture by e.g. distillation, for reuse for the reaction.

In the above reaction (3), the compound (d) may be pyrolyzed in a gas phase at a temperature of from 150 to 250° C. in the presence of sodium carbonate or pyrolyzed in a gas phase at a temperature of from 250 to 400° C. in the presence of glass beads, whereby the compound ($m0_0$) can be obtained. Otherwise, the compound (d) is reacted with $M^CHCO_3$ or $M^C_2CO_3$ (wherein $M^C$ is an alkali metal atom) to convert the —COF group to a —COOM$^C$ group, followed by drying and then pyrolysis by heating at a temperature of from 150 to 300° C., preferably from 180 to 270° C., whereby the compound ($m0_0$) can be obtained. After converting the —COF group of the compound (d) to a —COOM$^C$ group, the compound may be pyrolyzed in an aprotic dry solvent. In such a case, the same solvent as in the above reaction (1) may be used. The pyrolitic temperature in such a case is from about 70 to 200° C.

In a case where the pyrolitic temperature is lower than about 250° C., the following compound ($m0_0$-z) may sometimes be formed as a by-product. This compound is considered to be derived from the following compound (d-z) formed as a by-product during the above reaction (1). Namely, it is considered that hexafluoropropene oxide is added to the compound (d-z), followed by pyrolysis, to form the compound ($m0_0$-z). The compound ($m0_0$-z) is likely to impair the heat resistance of the polymer. Therefore, in a case where the compound ($m0_0$-z) is formed as a by-product, it is preferred to suppress the formation of such a compound by carrying out the pyrolysis of the compound (d) at a high temperature of from about 250 to 350° C. A gas phase pyrolysis is preferably employed. Further, it is also possible to remove the compound ($m0_0$-z) by thermally treating the compound ($m0_0$) containing the compound ($m0_0$-z) at a high temperature of from about 250 to 350° C. In a case where units ($m0_0$-z) have been included in the polymer, it may be possible that the polymer is thermally treated at a high temperature of from 250 to 350° C. to decompose the unstable moieties for stabilization.

(d-z)

The compound (m0₁) (the compound (m0) wherein n=1) in the present invention may be prepared by carrying out the following reaction following the above reaction (1).

(4) the compound (d) is reacted with a compound (e) in the presence of $M^bF$ (where $M^b$ is an alkali metal atom) in an amount of at least about equimolar to the compound (d).

As $M^bF$, potassium fluoride is particularly preferred. In the compound (e), X is —OSO₂F, —I, —Cl or —Br, particularly preferably —OSO₂F in view of the high reactivity. As the solvent, the same solvent as in the above reaction (1) may be used. The reaction temperature is from −50° C. to +100° C., preferably from −20° C. to +50° C.

In the present invention, a polymer may be produced by polymerizing the compound (m0). The polymer is a polymer (hereinafter referred to as the polymer (m0)) comprising units (m0) based on the compound (m0).

The polymer (m0) is preferably a polymer (m1) comprising units (m1) based on a compound (m1).

The polymer (m0) of the present invention may be a polymer comprising at least one type of units (m0) or a polymer comprising at least one type of units (m0) and at least one type of units (hereinafter referred to as other units) other than the units (m0). The latter polymer (m0) is preferably a polymer comprising one type of units (m0) and at least one type of other units. The polymer (m0) as a polymer having other units is preferably one prepared by a method of copolymerizing the compound (m0) with copolymerizable other monomers.

As such other monomers, nonionic monomers are usually selected. Here, non-ionic means that the monomers have no ionic groups or precursor groups thereof. Examples of such other monomers include tetrafluoroethylene, chlorotrifluoroethylene, trifluoroethylene, vinylidene fluoride, vinyl fluoride and ethylene. Examples of a monomer having a cyclic structure among other monomers include perfluoro(2,2-dimethyl-1,3-dioxole), perfluoro(1,3-dioxole), perfluoro(2-methylene-4-methyl-1,3-dioxolane) and perfluoro(4-methoxy-1,3-dioxole). Examples of a cyclopolymerizable monomer among other monomers include perfluoro(3-butenyl vinyl ether), perfluoro(allyl vinyl ether) and perfluoro(3,5-dioxa-1,6-heptadiene). Further, the following monomers (wherein p is an integer of from 2 to 6) may also be suitably used.

Among the above-mentioned other monomers, tetrafluoroethylene is preferred, since its copolymer will not only be excellent in chemical stability and heat resistance but also have a high mechanical strength, and the softening temperature of the copolymer will also be higher than a conventional sulfonic acid polymer.

Further, as a monomer which is further copolymerizable together with the above exemplified other monomers, propene, a perfluoro α-olefin such as hexafluoropropene, a (perfluoroalkyl)ethylene such as (perfluorobutyl)ethylene, a (perfluoroalkyl)propene such as 3-perfluorooctyl-1-propene, perfluoro(alkyl vinyl ether) or a perfluorovinyl ether such as a perfluoro(etheric oxygen atom-containing alkyl vinyl ether) may, for example, be used.

The comonomer of a perfluorovinyl ether is preferably a compound represented by $CF_2=CF-(OCF_2CFZ)_t-O-Rf$, where t is an integer of from 0 to 3, Z is a fluorine atom or a trifluoromethyl group, and Rf is a $C_{1-12}$ perfluoroalkyl group which may have a linear structure or a branched structure. Particularly preferred are the following compounds (i) to (iii). In the formulae, v is an integer of from 1 to 9, w is an integer of from 1 to 9, and x is 2 or 3.

In order to obtain a polymer capable of forming an electrolyte material excellent in chemical stability with high durability for a polymer electrolyte fuel cell, it is preferred to select perfluorocompounds as the above-mentioned other monomers.

It is effective to introduce a cyclic structure into a polymer in order to obtain a polymer to be used as a polymer electrolyte having high oxygen solubility or oxygen permeability to be applied to a cathode catalyst layer in order to increase the cell output or as a polymer electrolyte membrane having a still higher softening temperature as compared with a polymer obtainable by copolymerizing the compound (m0) with tetrafluoroethylene, in a fuel cell. In such a case, it is preferred to select, as other monomers, the above-mentioned monomers containing a cyclic structure or cyclopolymerizable monomers. Among them, perfluoro(2,2-dimethyl-1,3-dioxole) is preferred.

In a case where other units are contained in the polymer of the present invention, the proportion of such other units is selected so that the ion exchange capacity will be in the after-mentioned range. In a case where the polymer is used for an electrolyte membrane of a fuel cell, such other units are preferably tetrafluoroethylene units as mentioned above, but in order to control the softening temperature or the moldability, other units may be contained as a third component. The third component is preferably units based on a monomer having a cyclic structure or a cyclopolymerizable monomer. In order to maintain the membrane strength, the tetrafluoroethylene units are preferably contained in an amount of at least 20 mol %, more preferably at least 40 mol %. Also in a case where the polymer of the present invention is used for a catalyst layer for a fuel cell, a polymer having the same composition as for the membrane may be employed. The third component is preferably units based on a monomer having a cyclic structure or a cyclopolymerizable monomer. Further, it is possible to use a polymer containing, as other units, units based on a monomer having a cyclic structure or a cyclopolymerizable monomer and not containing tetrafluoroethylene units. However, in order to obtain a constant performance over a long period of time, it is preferred to employ a polymer containing at least 20 mol %, more preferably at least 40 mol % of tetrafluoroethylene units.

The polymerization reaction is not particularly limited so long as it is carried out under such a condition that radicals will be formed. For example, it may be carried out by bulk polymerization, solution polymerization, suspension polymerization, emulsion polymerization, or polymerization in liquid or supercritical carbon dioxide.

The method for generating radicals is not particularly limited. For example, a method of irradiating radiation such as ultraviolet rays, γ-rays or electron rays may be employed, or a method of using a radical initiator which is commonly used for radical polymerization may be employed. The reaction temperature for polymerization reaction is also not particularly limited. For example, it is usually at a level of from 10 to 150° C. In the case of the compound (m1) wherein n=0, it is preferably polymerized at a temperature of from 15 to 80° C. If the temperature becomes too high, a chain transfer tends to take place by a disproportionation reaction due to self-rearrangement of propagating terminal radicals as shown by the following formula, whereby the molecular weight tends to be hardly increased.

In the case of the compound (m1) wherein n=1, the polymerization reactivity is low as compared with the compound wherein n=0 and accordingly, it is preferred to carry out the polymerization in a slightly higher temperature region of from 60 to 120° C. in order to increase the reactivity.

In a case where a radical initiator is used, such a radical initiator may, for example, be a bis(fluoroacyl) peroxide, a bis(chlorofluoroacyl) peroxide, a dialkylperoxy dicarbonate, a diacyl peroxide, a peroxy ester, a dialkyl peroxide, a bis(fluoroalkyl) peroxide, an azo compound or a persulfate.

In a case where solution polymerization is carried out, the solvent to be used usually preferably has a boiling point of from 20 to 350° C., more preferably has a boiling point of from 40 to 150° C., from the viewpoint of the handling efficiency. And, one or more of the above monomers will be put in the solvent, and a radical initiator, etc. will be added to generate radicals thereby to carry out polymerization. The addition of a gas monomer and/or a liquid monomer may be an addition all at once, sequential addition or continuous addition.

Here, a useful solvent may, for example, be a perfluorotrialkylamine such as perfluorotributylamine, a perfluorocarbon such as perfluorohexane or perfluorooctane, a hydrofluorocarbon such as 1H,4H-perfluorobutane or 1H-perfluorohexane, or a hydrochlorofluorocarbon such as 3,3-dichloro-1,1,1,2,2-pentafluoropropane or 1,3-dichloro-1,1,2,2,3-pentafluoropropane.

The suspension polymerization may be carried out by adding monomers to be polymerized, to water as a dispersion medium and using, as a radical initiator, a non-ionic initiator such as a bis(fluoroacyl) peroxide, a bis(chlorofluoroacyl) peroxide, a dialkylperoxy dicarbonate, a diacyl peroxide, a peroxyester, a dialkyl peroxide, a bis(fluoroalkyl) peroxide or an azo compound. A solvent described in the section for the solution polymerization may be added as an assisting agent. Further, in order to prevent agglomeration of suspended particles, a surfactant may optionally be added as a dispersion stabilizer.

For the adjustment of the molecular weight, a hydrocarbon compound such as hexane or methanol may be added.

The compound (m0) wherein n=1 has a $CF_2$=$CFCF_2O$— group as the polymerizable moiety, and a polymer obtained by polymerizing such a compound is preferably thermally treated. A polymer of the monomer having a $CF_2$=$CFCF_2O$— group has similar repeating units of the following formula (Iv) to those of the copolymer (hereinafter referred to as "FEP") of tetrafluoroethylene with hexafluoropropene (hereinafter referred to as "HFP") and has a low heat resistance like FEP. In the case of FEP, the polymer obtained by polymerization by itself is known to undergo a change in the melt viscosity (molecular weight) or formation of bubbles during the mold processing. This is attributable to thermally unstable polymer main chain or terminals, and in FEP, this is particularly attributable to weak HFP—HFP bonds in its main chain. As a measure to cope with such a problem, it has been common to treat the polymer at a high temperature of from 200 to 400° C. or to exert a high shearing force in a twin screw extruder to cut weak bond portions (Fluororesin Handbook, The Nikkan Kogyo Shimbun, Ltd. (1990), II. Fluororesin 2.

Tetrafluoroethylene/hexafluoropropylene copolymer (FEP), p. 213). Therefore, it is considered that also in the case of a polymer of the monomer having a $CF_2$=$CFCF_2O$— group, it is preferred to carry out the same thermal treatment as for FEP.

(iv)

The polymer of the present invention may be subjected to thermal treatment in the presence of air and/or water after the polymerization, or fluorination with fluorine gas, to stabilize unstable moieties such as polymer ends, in order to improve the durability, etc.

The weight average molecular weight of the polymer having —$SO_2F$ groups of the present invention is preferably from $1\times10^4$ to $1\times10^7$, particularly preferably from $5\times10^4$ to $5\times10^6$, further preferably from $1\times10^5$ to $3\times10^6$. If the molecular weight of the polymer is too small, the physical properties such as the swelling degree are likely to change with time, whereby the durability is likely to be inadequate. On the other hand, if the molecular weight is too large, solubilization or molding is likely to be difficult.

The polymer having —$SO_2F$ groups of the present invention can be converted to a polymer containing sulfonate groups or sulfonic acid groups (—$SO_3H$ groups) by hydrolysis in the presence of a base, or by hydrolysis, followed by treatment for an acid form. Such a polymer is suitable as a polymer electrolyte. An ionic group-containing polymer thus obtained may be treated with an aqueous hydrogen peroxide solution as the case requires. Such a method for conversion of the groups or polymer treatment may be carried out by conventional methods and conditions.

In the polymer of the present invention, two sulfonic acid groups in one unit are not bonded to the same carbon atom. If the two sulfonic acid groups are bonded to the same carbon atom, the distance between the adjacent —$CF(SO_3H)_2$ groups in the polymer molecule tends to be inversely large, whereby proton transmission between the sulfonic acid groups tends to be not so easy, and the effect to improve the proton conductivity is considered to be not high. On the other hand, with the polymer of the present invention, the two sulfonic acid groups in one unit are properly apart via e.g. a perfluoroalkylene structure, whereby it is considered that the distances between the respective sulfonic acid groups in the polymer molecule will be uniform, and mobility of protons will be easy, such being desirable.

The polymer having —$SO_3H$ groups of the present invention preferably has a softening temperature of at least 90° C., more preferably at least 100° C. Here, the softening temperature of the polymer is the temperature at which the elastic modulus of the polymer starts to rapidly decrease when the polymer is gradually heated from about room temperature and is defined to be a temperature at which the storage modulus becomes one-half of the value at 50° C. when the dynamic viscoelasticity is measured at a measuring frequency of 1 Hz at a temperature raising rate of 2° C./min.

The polymer having —$SO_3H$ groups preferably has an ion exchange capacity (hereinafter referred to as $A_R$) of from 0.5 to 2.5 meq/g dry polymer (hereinafter referred to as meq/g). If $A_R$ of the polymer is too small, the water content of the polymer tends to be low, and the ion conductivity tends to be low. Accordingly, when the polymer is used as a material constituting a catalyst layer or a polymer electrolyte membrane for a polymer electrolyte fuel cell, it tends to be difficult to obtain sufficient cell output. On the other hand, if $A_R$ of the polymer is too large, preparation of the polymer having a high molecular weight is not easy, and the polymer tends to be excessively swelled with water, whereby it tends to be difficult to maintain the strength.

From the above viewpoint, $A_R$ of the polymer having —$SO_3H$ groups of the present invention is more preferably from 0.9 to 2.3 meq/g, further preferably from 1.4 to 2.1 meq/g. As a polymer having only one —$SO_3H$ group in a side chain, which is commonly employed, one having $A_R$ of from 0.9 to 1.1 meq/g is used from the balance of the resistance and the strength. Whereas, the polymer having two —$SO_3H$ groups in a side chain, of the present invention is capable of maintaining the mechanical strength even if the ion exchange capacity is made large to have the resistance less than that of the conventional membrane.

The polymer having —$SO_3H$ groups of the present invention is useful as a polymer electrolyte for various applications without being limited to electrolysis of sodium chloride or to application to a fuel cell. In this specification, polymer electrolyte material is meant for a polymer material to be used by utilizing functions of ionic groups, and the ionic groups have an ion conducting function, an ion exchange function, a water-absorbing function, etc., and when the material contains strongly acidic groups, it has an acid catalyst function. It may be used also for a proton selective permeation membrane to be used for electrolysis of water, production of hydrogen peroxide, production of ozone, recovery of a waste acid, etc., for a diaphragm of a redox flow cell, or a cation exchange membrane for electrodialysis to be used for desalination or salt production. Further, it may be used also as a polymer electrolyte for a lithium is primary cell, a lithium secondary cell or a lithium ion secondary cell or a solid acid catalyst, a cation exchange resin, a sensor employing a modified electrode, an ion exchange filter to remove a trace amount of ions in air, or an actuator, or an electrochromic display element. Namely, it may be used as a material for various electrochemical processes.

Further, the polymer having —$SO_3H$ groups of the present invention may be used as a solid acid catalyst. In such a case, if its softening temperature is high, the reaction temperature can be made high, and a desired reaction may be carried out in a higher temperature range. The polymer having —$SO_3H$ groups of the present invention can be made to have a large ion exchange capacity, and it is possible to introduce reaction active sites more than a conventional polymer.

Further, the polymer having —$SO_3H$ groups of the present invention may be used for a membrane for diffusion dialysis to be used for separation and purification of acids, bases and salts, a charged porous membrane for separating proteins (such as a charged reverse osmosis membrane, a charged ultrafiltration membrane, a charged microfiltration membrane, etc.), a dehumidifying membrane, a humidifying membrane, etc. Further, it may be used as an agent to impart hydrophilicity to a filter made of a PTFE porous material.

EXAMPLES

Now, the present invention will be described in further detail with reference to Examples, but it should be understood that the present invention is by no means restricted thereto.

Abbreviations employed are as follows.
HCFC 225cb: $CClF_2CF_2CHClF$
PSVE: $CF_2$=$CFOCF_2CF(CF_3)OCF_2CF_2SO_2F$
AIBN: $(CH_3)_2C(CN)N$=$NC(CH_3)_2(CN)$ IPP: $(CH_3)_2CHOC(=O)OOC(=O)OCH(CH_3)_2$
HCFC 141b: $CH_3CCl_2F$
TFE: $CF_2=CF_2$

PFBPO:

Measurements of the physical properties of a polymer were carried out as follows.

A TQ value was measured as an index for the molecular weight of a polymer. The TQ value (unit: °C.) is a temperature at which the extrusion amount becomes 100 mm³/sec when melt extrusion of a polymer was carried out under a condition of an extrusion pressure of 2.94 MPa by using a nozzle having a length of 1 mm and an inner diameter of 1 mm. The extrusion amount was measured by changing the temperature by means of Flow Tester CFT-500A (manufactured by Shimadzu Corporation), and a TQ value at which the extrusion amount becomes 100 mm³/sec, was obtained.

The polymer composition was obtained by quantitatively analyzing the fluorosulfonyl group by an infrared absorption spectrum.

$A_R$ of a polymer was obtained as follows. With respect to a copolymer of TFE with the compound (m11), the polymer F12 was hydrolyzed by immersing it in a solution having a predetermined concentration of NaOH in a solvent of water/methanol, and $A_R$ was obtained by back titration of the solution. With respect to the other polymers of a copolymer of TFE with the compound (m11), it was obtained by comparing the absorption intensity of the fluorosulfonyl group in the infrared absorption spectrum with that of the polymer F4. With respect to a copolymer of TFE with the compound (m12), $A_R$ was obtained by hydrolysis/back titration of the polymer F20, and with respect to the other polymers, it was obtained by the infrared absorption spectrum. With respect to a copolymer of TFE with PSVE, $A_R$ was obtained by hydrolysis/back titration of the polymers F101 to 103.

Measurement of the softening temperature was carried out as follows. A polymer obtained by polymerization was pressed at a temperature in the vicinity of TQ to obtain a film having a thickness of from about 100 to 200 μm. Such a film was subjected to alkali hydrolysis and then converted to an acid form polymer by acid treatment. By using a dynamic viscoelasticity measuring apparatus DVA200 (manufactured by ITK Co., Ltd.), the dynamic viscoelasticity of the above-mentioned acid form film was measured with a sample width of 0.5 cm, and a length between chucks of 2 cm at a measurement frequency of 1 Hz at a temperature raising rate of 2° C./min and a temperature at which the storage modulus becomes one-half of the value at 50° C. was taken as the softening temperature.

The specific resistivity was measured by a known four terminal method by closely contacting a substance having four terminal electrodes disposed at intervals of 5 mm to a film having a width of 5 mm under constant temperature and humidity conditions of 80° C. and 95% RH within an alternate current of 10 kHz at a voltage of 1 V.

Example 1

Preparation of Compound (M11)

The compound (m11) was prepared by the following synthetic route. The details will be described below. The compound (s1) was prepared in the same manner as the method disclosed in JP-A-2002-528433 (Example 1).

(1) Preparation of Compound (a1)

In an autoclave (internal capacity: 200 cm³), the compound (s1) (300 g) was charged, and an oxidation reaction was carried out by bubbling oxygen gas while the internal temperature was maintained from 100° C. to 101.5° C. At the time when the internal pressure of the autoclave rose to 1.0 MPa (gauge pressure) along with bubbling, the bubbling was terminated, and the internal temperature was cooled to 25° C., whereupon the internal pressure was purged.

Successively, the oxidation reaction was repeatedly carried out until in the ¹⁹F-NMR analysis of the solution in the autoclave, the ratio of the sum of areas of spectra attributable to fluorine atoms bonded to a carbon-carbon unsaturated bond to the sum of areas of spectra attributable to all fluorine atoms bonded to carbon atoms became at most 0.05, to obtain a compound (a1) (yield: 260 g).

¹⁹F-NMR of compound (a1) (282.7 MHz, solvent: CDCl₃, standard: CFCl₃) δ (ppm): 46.24 (1F), −109.45 (1F), −109.75 (2F), −112.55 (1F), −152.55 (1F), −118.10 to −124.19 (2F).

(2) Preparation of Compound (c1)

Into a 200 cm³ glass flask equipped with a stirrer, a dropping funnel and a Dimroth condenser, potassium fluoride (tradename: Chloro-catch F, manufactured by MORITA CHEMICAL INDUSTRIES Co., Ltd.) (6.4 g) and monoglyme (51 g) were put and stirred, and while the internal temperature was cooled at from 5 to 10° C., from the dropping funnel, tetrafluoroethane-β-sultone (compound (b11)) (20 g) was dropwise added. After the dropwise addition, stirring was continued for 30 minutes, and then, from the dropping funnel, the compound (a1) (28 g) was dropwise added at from 10 to 20° C. After the dropwise addition, the mixture was stirred at 20° C. for 20 hours. After completion of the reaction, distillation under reduced pressure was carried out to obtain 43.2 g of a fraction of 75° C./4 kPa (absolute pressure). The purity by gas chromatography (hereinafter referred to as GC) was 98%.

$^{19}$F-NMR of compound (c1) (282.7 MHz, solvent: CDCl$_3$, standard: CFCl$_3$) δ (ppm): 46.5 (1F), 45.8 (1F), 27.9 (1F), −77.1 (1F), −85.5 (1F), −107.6 (2F), −112.5 (2F), −118.8 (2F), −128.0 (1F).

(3) Preparation of Compound (d1)

Into a 200 cm$^3$ stainless steel autoclave equipped with a stirrer and a pressure gauge, potassium fluoride (tradename: Chloro-catch F, manufactured by MORITA CHEMICAL INDUSTRIES Co., Ltd.) (1.2 g), monoglyme (9.6 g), the compound (c1) (92 g) were added and stirred at from 5 to 10° C. for one hour. Thereafter, under a pressure of at most 0.2 MPa (gauge pressure), hexafluoropropene oxide (33 g) was continuously added. After completion of the addition, stirring was continued for two hours, and then, the reaction solution was separated by a separatory funnel to obtain 121 g of a fluorocarbon layer.

By distillation, 86.6 g of a fraction of 60° C./0.33 kPa (absolute pressure) was obtained. The GC purity of the fraction was 94%. The major by-product was a compound having two mol of hexafluoropropene oxide added.

$^{19}$F-NMR of compound (d1) (282.7 MHz, solvent: CDCl$_3$, standard: CFCl$_3$) δ (ppm): 46.4 (1F), 45.3 (1F), 26.7 (1F), −76.6 (1F), −79.0 (2F), −82.2 (3F), −83.7 (1F), −107.0 (1F), −108.6 (1F), −112.4 (2F), −118.5 (2F), −131.1 (1F), −140.4 (1F).

(4) Preparation of Compound (m11)

Using a stainless steel tube having an inner diameter of 1.6 cm, a U-tube having a length of 40 cm was prepared. In one side, a glass wool was packed, and in another side, glass beads were packed using a stainless steel sintered metal as a perforated plate to form a fluidized-bed reactor. Using nitrogen gas as a fluidizing gas, the starting material was continuously supplied by using a metering pump. The outlet gas was collected by liquid nitrogen by means of a trap tube.

The above U-tube was put in a salt bath, and at the reaction temperature of 330° C., the compound (d1) (63 g) was supplied over a period of 3 hours. The molar ratio of compound (d1)/N$_2$ at that time was 1/20.

After completion of the reaction, from the liquid nitrogen trap, 47.4 g of a liquid was obtained. The GC purity was 85%. By distillation, as a fraction of boiling point 66° C./0.67 kPa (absolute pressure), 25 g of the compound (m11) was obtained. The GC purity was 99%.

$^{19}$F-NMR of monomer (m11) (282.7 MHz, solvent: CDCl$_3$, standard: CFCl$_3$) δ (ppm): 46.3 (1F), 45.4 (1F), −79.1 (2F), −82.8 (2F), −106.7 (1F), −108.4 (1F), −112.3 (2F), −112.7 (dd, J=82.2 Hz, 66.9 Hz, 1F), −118.5 (2F), −121.3 (dd, J=112.7 Hz, 82.2 Hz, 1F), −136.2 (ddt, J=112.9 Hz, 67.1 Hz, 6.0 Hz, 1F), −140.2 (1F).

Example 2

Preparation of compound (m12)

The compound (m12) was prepared by the following synthetic route. The details will be described below. The compound (a2) was prepared in the same manner as the method disclosed in JP-A-57-176973 (Example 2). Otherwise, the compound (a2) may be prepared by the following method.

Preparation of Compound (a2)

Using a 0.2 L autoclave made of hastelloy C and equipped with a stirrer provided with stirring vanes, a liquid/gas inlet, a product outlet and a condenser, 128 g of CF$_2$=CFCF$_2$OCF$_2$CF$_2$SO$_2$F was charged. Then, with stirring by the stirrer at 250 rpm, the reactor was heated to 110° C., and 5 L/min of oxygen gas and 20 L/min of nitrogen gas were introduced into the reactor. The reaction pressure was maintained to be 3.0 MPa (gauge pressure) by using a back pressure valve. The reaction mixture was refluxed by the condenser, and the gas was discharged via the back pressure valve out of the reactor. The reaction was carried out while the conversion of the starting material compound was checked, and the checking of the conversion was carried out by withdrawing a part of the reaction mixture from the product outlet. The analysis of the reaction product was carried out by gas chromatography. The oxygen gas was charged until the conversion of the starting material compound became 90%. The reaction time required 16 hours, the yield of the compound (a2) was 73%, and the selectivity was 81%.

(1) Preparation of Compound (c2)

A 300 cm$^3$ four-necked round bottomed flask equipped with a Dimroth condenser, a thermometer, a dropping funnel and a stirring vane-attached glass rod, was prepared. In a nitrogen atmosphere, potassium fluoride (tradename: Chlorocatch F, manufactured by MORITA CHEMICAL INDUSTRIES Co., Ltd.) (1.6 g) and dimethoxy ethane (15.9 g) were added into the reactor.

Then, the reactor was cooled with an ice bath, and from the dropping funnel, tetrafluoroethane-β-sultone (compound (b11)) 49.1 g was dropwise added over a period of 32 minutes at an internal temperature of at most 10° C. After completion of the dropwise addition, the compound (a2) (82.0 g) was dropwise added over a period of 15 minutes from the dropping funnel into the reactor. No substantial rise of the internal temperature was observed. After completion of the dropwise addition, the temperature was returned to room temperature, and stirring was continued for about 90 hours. By a separatory funnel, the lower layer was recovered. The recovered amount was 127.6 g, and the GC purity was 55%.

The recovered liquid was transferred to a 200 cm³ four-necked round bottomed flask, and distillation was carried out. Under a reduced pressure of from 1.0 to 1.1 kPa (absolute pressure), 97.7 g of the main fraction was obtained. The GC purity was 98%, and the yield was 80%.

$^{19}$F-NMR of compound (c2) (282.7 MHz, solvent: CDCl$_3$, standard: CFCl$_3$) δ (ppm): 45.6 (2F), 27.4 (1F), −77.7 (1F), −82.5 (2F), −84.0 (2F), 85.1 (1F), −112.5 (2F), −112.8 (2F), −130.5 (1F).

(2) Preparation of Compound (d2)

Into a stainless steel autoclave having an internal capacity of 200 cm³, potassium fluoride (tradename: Chloro-catch F, manufactured by MORITA CHEMICAL INDUSTRIES Co., Ltd., hereinafter referred to as simply as "KF") (1.1 g) was added. After deaeration, under reduced pressure, dimethoxy ethane (5.3 g), acetonitrile (5.3 g) and the compound (c2) (95.8 g) were added.

Then, the reactor was cooled with an ice bath, and at an internal temperature of from 0 to 5° C., hexafluoropropene oxide (27.2 g) was added over a period of 27 minutes, and then, the temperature was returned to room temperature with stirring, and the stirring was continued overnight. By a separatory funnel, the lower layer was recovered. The recovered amount was 121.9 g, and the GC purity was 63%. By distillation, as a fraction of boiling point of 80 to 84° C./0.67 to 0.80 kPa (absolute pressure), 72.0 g of the compound (d2) was obtained. The GC purity was 98%, and the yield was 56%.

$^{19}$F-NMR of compound (d2) (282.7 MHz, solvent: CDCl$_3$, standard: CFCl$_3$) δ (ppm): 45.6 (1F), 45.2 (1F) 26.7 (1F), −77.8 (1F), −79.5 (2F), −82.2, −82.3 (2 peaks together 7F), −85.0 (1F), −112.4 (2F), −112.7 (2F), −131.2 (1F), −145.0 (1F).

(3) Preparation of Compound (m12) (First Preparation)

A 50 cm³ two-necked round bottomed flask equipped with a thermometer, a dropping funnel and a stirring bar, was prepared. In a nitrogen atmosphere, into the reactor, potassium hydrogen carbonate (1.02 g) and dimethoxy ethane (8.78 g) were added. Then, the flask was cooled by immersing in an ice bath, and at an inner temperature of from 4 to 11° C., 7.05 g of the compound (d2) was dropwise added over a period of 21 minutes from the dropping funnel. After completion of the dropwise addition, the ice bath was removed, and stirring was continued at room temperature for 2.5 hours.

By a rotary evaporator, the solvent was distilled off, and vacuum drying was carried out at 80° C. for 14 hours, at 100° C. for 5.5 hours and at 120° C. for 10.5 hours. After drying, 6.71 g of a potassium salt was obtained.

In the same manner, from the compound (d2) (64.5 g), 52.8 g of the potassium salt was obtained.

Then, a simple distillation apparatus was attached to a 50 cm³ two-necked round bottomed flask equipped with a thermometer. Into the reaction system, 6.6 g of the potassium salt was introduced. Under reduced pressure, the reactor was gradually heated by an oil bath. At an oil bath temperature of from 190 to 230° C., 4.34 g of a liquid fraction (GC purity: 87.8%) was recovered over a period of about one hour. In the same manner, from 52.4 g of the potassium salt, at an oil bath temperature of from 190 to 250° C., 40.2 g of a liquid fraction (GC 87%) was recovered over a period of about one hour.

These two fractions were put together and subjected to distillation, whereby the compound (m12) (26.7 g) was obtained as a fraction of boiling point of from 73 to 74° C./0.67 kPa (absolute pressure). The GC purity was 92%. It was analyzed by GC-MS (gas chromatograph-mass spectrometry), whereby it was found to contain 3% of each of the compounds which are considered to be the following isomer (p) and an impurity (q).

(4) Preparation of Compound (m12) (Second Preparation)

In the same manner as the preparation of the compound (m11), using the fluorized bed reaction apparatus, the compound (d2) (34.6 g) was supplied over a period of 1.5 hours at a reaction temperature of 340° C.

After completion of the reaction, 27 g of a reaction product was obtained from the liquid nitrogen trap. The GC purity was 84%. By distillation, as a fraction of boiling point of 69° C./0.40 kPa, the compound (m12) was obtained. The GC purity was 98%.

$^{19}$F-NMR of compound (m12) (282.7 MHz, solvent: CDCl$_3$, standard: CFCl$_3$) δ (ppm): 45.5 (1F), 45.2 (1F), −79.5 (2F), −82.4 (4F), −84.1 (2F), −112.4 (2F), −112.6 (2F), −112.9 (dd, J=82.4 Hz, 67.1 Hz, 1F), −121.6 (dd, J=112.9 Hz, 82.4 Hz, 1F), −136.0 (ddt, J=112.9 Hz, 67.1 Hz, 6.1 Hz, 1F), −144.9 (1F).

Example 3

Preparation of Polymer

Into an autoclave (internal capacity: 100 cm³, made of stainless steel), the compound (m11) (35.22 g), HCFC 225cb (28.78 g) and IPP (11.9 mg) were put, cooled by liquid nitrogen and deaerated. The internal temperature was raised to 40° C., and TFE was introduced into the autoclave to bring the pressure to 0.3 MPaG (gauge pressure). While the temperature and pressure were maintained to be constant, polymerization was carried out for 25.6 hours. Then, the interior of the autoclave was cooled to terminate the polymerization, and the gas in the system was purged.

The reaction solution was diluted with HCFC 225cb, and then HCFC 141b was added to flocculate the polymer, followed by filtration. Then, the polymer was stirred in HCFC 225cb and re-flocculated by HCFC 141b. Drying under reduced pressure at 80° C. was carried out overnight to obtain a polymer F11. The obtained amount was 12.2 g.

The content of units (m11) obtained by IR was 17.8 mol %. The TQ value was 237° C.

Examples 4 to 7

Preparation of Polymers

TFE and the compound (m11) were copolymerized in the same manner as in Example 3 except that in Example 3, respective conditions were changed as shown in Table 1, to obtain polymers F12 to F15. The polymerization results are shown in Table 1.

Examples 8 to 12

Preparation of polymers

TFE and the compound (m12) were copolymerized in the same manner as in Example 3 except that in Example 3, respective conditions were changed as shown in Table 2, to obtain polymers F16 to F20. The polymerization results are shown in Table 2.

TABLE 1

| | Example | | | | |
|---|---|---|---|---|---|
| | 3 | 4 | 5 | 6 | 7 |
| Obtained polymer | F11 | F12 | F13 | F14 | F15 |
| Volume of reactor (cm$^3$) | 100 | 100 | 30 | 30 | 30 |
| Monomer (m11) (g) | 35.22 | 53.81 | 9.02 | 8.99 | 6.75 |
| HCFC 225cb (g) | 28.78 | 10.30 | 7.45 | 7.35 | 5.15 |
| Initiator | IPP | AIBN | IPP | IPP | AIBN |
| Amount of initiator (mg) | 11.9 | 6.5 | 7.8 | 7.7 | 3.4 |
| Polymerization temperature (° C.) | 40 | 67 | 40 | 40 | 70 |
| Pressure (MpaG) | 0.30 | 1.23 | 0.44 | 0.54 | 1.37 |
| Polymerization time (hrs) | 25.6 | 10.0 | 4.2 | 4.8 | 6.2 |
| Yield (g) | 12.2 | 11.4 | 1.4 | 3.0 | 5.1 |
| $A_R$ (meq · g$^{-1}$) | 1.96 | 1.86 | 1.70 | 1.51 | 1.06 |
| Unit (m11) (mol %) | 17.8 | 16.3 | 14.0 | 11.6 | 7.0 |
| TQ (° C.) | 237 | 237 | 270 | 310 | 351 |

TABLE 2

| | Example | | | | |
|---|---|---|---|---|---|
| | 8 | 9 | 10 | 11 | 12 |
| Obtained polymer | F16 | F17 | F18 | F19 | F20 |
| Volume of reactor (cm$^3$) | 30 | 30 | 30 | 30 | 30 |
| Monomer (m12) (g) | 9.84 | 8.51 | 8.16 | 9.43 | 11.8 |
| HCFC 225cb (g) | 3.09 | 4.03 | 4.21 | 4.85 | 5.58 |
| Initiator | AIBN | IPP | IPP | IPP | AIBN |
| Amount of initiator (mg) | 1.3 | 0.63 | 6.1 | 7.2 | 1.8 |
| Polymerization temperature (° C.) | 70 | 40 | 40 | 40 | 65 |
| Pressure (MpaG) | 1.31 | 0.57 | 0.63 | 0.71 | 1.11 |
| Polymerization time (hrs) | 5.7 | 10.0 | 2.1 | 2.8 | 9.0 |
| Yield (g) | 1.2 | 0.98 | 0.80 | 2.1 | 2.1 |
| $A_R$ (meq · g$^{-1}$) | 1.63 | 1.29 | 1.13 | 0.86 | 1.51 |
| Unit (m12) (mol %) | 14.3 | 9.8 | 8.1 | 5.6 | 12.5 |
| TQ (° C.) | 225 | 320 | 270 | 279 | 270 |

Examples 13 to 21

Preparation of Acid-Form Polymers

Polymers F11 to F19 obtained in Examples 3 to 11 were, respectively, treated by the following method to obtain films of acid-form polymers H11 to H19. Firstly, polymer F15 was formed at a temperature of 320° C. and the other polymers were formed at the TQ temperature by press forming into the respective polymer films (film thicknesses of from 100 to 200 µm). Then, in an aqueous solution containing 30 mass % of dimethyl sulfoxide and 15 mass % of KOH, the polymer films were immersed at 80° C. for 16 hours, whereby —SO$_2$F groups in the polymer films were hydrolyzed and converted to —SO$_3$K groups.

Further, the polymer films were immersed in a 3 mol/L hydrochloric acid aqueous solution at 50° C. for two hours, and then the aqueous hydrochloric acid solution was changed to new one. Such acid treatment was repeated four times. Then, the polymer films were thoroughly washed with deionized water to obtain polymer films wherein —SO$_3$K groups were changed to —SO$_3$H groups.

The softening temperatures and specific resistivities of the acid form polymers were measured. The results are shown in Tables 3 and 4. Further, the glass transition temperature (Tg) obtained from the peak value of tan δ in the measurement of the dynamic viscoelasticity was also shown.

TABLE 3

| | Example | | | | |
|---|---|---|---|---|---|
| | 13 | 14 | 15 | 16 | 17 |
| Polymer used | F11 | F12 | F13 | F14 | F15 |
| Obtained polymer | H11 | H12 | H13 | H14 | H15 |
| Softening temperature (° C.) | 120 | 122 | 120 | 120 | 126 |
| Tg (tan δ) (° C.) | 146 | 150 | 150 | 150 | 150 |
| Specific resistivity (Ω · cm) | 1.4 | 1.7 | 1.9 | 2.1 | 4.3 |

TABLE 4

| | Example | | | |
|---|---|---|---|---|
| | 18 | 19 | 20 | 21 |
| Polymer used | F16 | F17 | F18 | F19 |
| Obtained polymer | H16 | H17 | H18 | H19 |
| Softening temperature (° C.) | 109 | 110 | 116 | 125 |
| Tg (tan δ) (° C.) | 138 | 136 | 136 | 138 |
| Specific resistivity (Ω · cm) | 2.3 | 3.1 | 3.1 | 6.0 |

Examples 22 to 24

TFE and PSVE were copolymerized to obtain polymers F101 to 103. They were further converted to acid forms to obtain polymers H101 to 103. The physical properties of the respective polymers were measured, and the results are shown in Table 5.

TABLE 5

| | Example | | |
|---|---|---|---|
| | 22 | 23 | 24 |
| Polymer | F101 | F102 | F103 |
| $A_R$ (meq · g$^{-1}$) | 1.10 | 1.00 | 0.91 |
| Units (PSVE) | 17.8 | 15.3 | 13.3 |

TABLE 5-continued

|  | Example | | |
|---|---|---|---|
|  | 22 | 23 | 24 |
| (mol %) | | | |
| TQ (° C.) | 225 | 220 | 220 |
| Polymer | H101 | H102 | H103 |
| Softening temperature (° C.) | 76 | 82 | 85 |
| Tg (tan δ) (° C.) | 109 | 110 | 112 |
| Specific resistivity (Ω · cm) | 3.6 | 4.8 | 6.6 |

Example 25

Preparation of Compound (m13)

The compound (c2) was prepared in the same manner as the synthetic route for the compound (m12) in Example 2, and then, from the compound (c2), the compound (m13) was prepared as follows. The details will be described below.

Into a 2,000 mL four-necked flask equipped with a thermometer, a Dimroth condenser and a stirrer, 677 g of diglyme was introduced into a nitrogen atmosphere. Then, with stirring, 23.33 g (402 mmol) of KF was added. A dropping funnel was attached to the reactor, and the reactor was cooled with an ice bath. 191.02 g (363 mmol) of the compound (c2) was dropwise added over a period of 30 minutes. During this period, the internal temperature was from 2.7 to 6.4° C. Stirring was continued for two hours under cooling in the ice bath.

Then, from the dropping funnel, 88.55 g (385 mmol) of $CF_2=CFOSO_2F$ was dropwise added over a period of 40 minutes. During this period, the internal temperature was from 0.9 to 3.4° C. Stirring was continued for three hours under cooling in the ice bath, and further, stirring was continued at room temperature overnight. The reaction solution was filtered, and then, of the two phases separated, the lower layer was recovered to obtain 218 g (purity 71.7%) of a crude product. And, by distillation under reduced pressure, the compound (m13) was obtained. Boiling point of 105-106° C./1.3-1.5 kPa. Isolation yield: 45%.

$^{19}F$-NMR of compound (m13) (282.7 MHz, solvent: $CDCl_3$, standard: $CFCl_3$) δ (ppm): 45.5 (1F), 45.1 (1F), −72.1 (2F), −79.6 (2F), −82.4 (4F), −82.9 (2F), −90.3 (1F), −104.2 (1F), −112.5 (2F), −112.7 (2F), −145.2 (1F), −190.8 (1F).

Examples 26 and 27

Preparation of Polymers

TFE and the compound (m13) were copolymerized in the same manner as in Example 3, except that in Example 3, the respective conditions were changed as shown in Table 6, to obtain polymer F26 and F27. The polymerization results are shown in Table 6. Further, with respect to the copolymer of TFE and the compound (m13), the ion exchange capacity was obtained by measuring the fluorescent X-ray intensity of sulfur atoms (apparatus used: RIX3000, manufactured by Rigaku Denki Kogyo K.K.) with respect to a film having a thickness of from 100 to 200 μm prepared by hot pressing. As the standard sample, a film of F101 was used.

TABLE 6

|  | Example | |
|---|---|---|
|  | 26 | 27 |
| Obtained polymer | F26 | F27 |
| Volume of reactor (cm³) | 30 | 30 |
| Monomer (m13) (g) | 24.92 | 25.08 |
| HCFC 225cb (g) | 0 | 0 |
| Initiator | PFBPO | PFBPO |
| Amount of initiator (mg) | 5.1 | 5.4 |
| Polymerization temperature (° C.) | 80 | 80 |
| Pressure (MpaG) | 0.25 | 0.14 |
| Polymerization time (hrs) | 8.5 | 9.0 |
| Yield (g) | 2.41 | 1.43 |
| $A_R$ (meq · g$^{-1}$) | 1.32 | 1.48 |
| Unit (m13) (mol %) | 10.7 | 12.9 |
| TQ (° C.) | 264 | 191 |

Examples 28 and 29

Preparation of Acid-Form Polymers and Measurement of Physical Properties

Polymers F26 and F27 obtained in Examples 26 and 27 were subjected to thermal treatment in air of 300° C. for 40 hours. Thereafter, the same treatment as in Examples 13 to 21 was carried out to obtain acid-form polymers H26 and H27. With respect to these polymers, measurement of the physical properties was carried out in the same manner as in Examples 13 to 21. The results are shown in Table 7.

TABLE 7

|  | Example | |
|---|---|---|
|  | 28 | 29 |
| Polymer used | F26 | F27 |
| Obtained polymer | H26 | H27 |
| Softening temperature (° C.) | 111 | 106 |
| Tg (tan δ) (° C.) | 134 | 138 |
| Specific resistivity (Ω · cm) | 3.0 | 2.3 |

Figure 1:
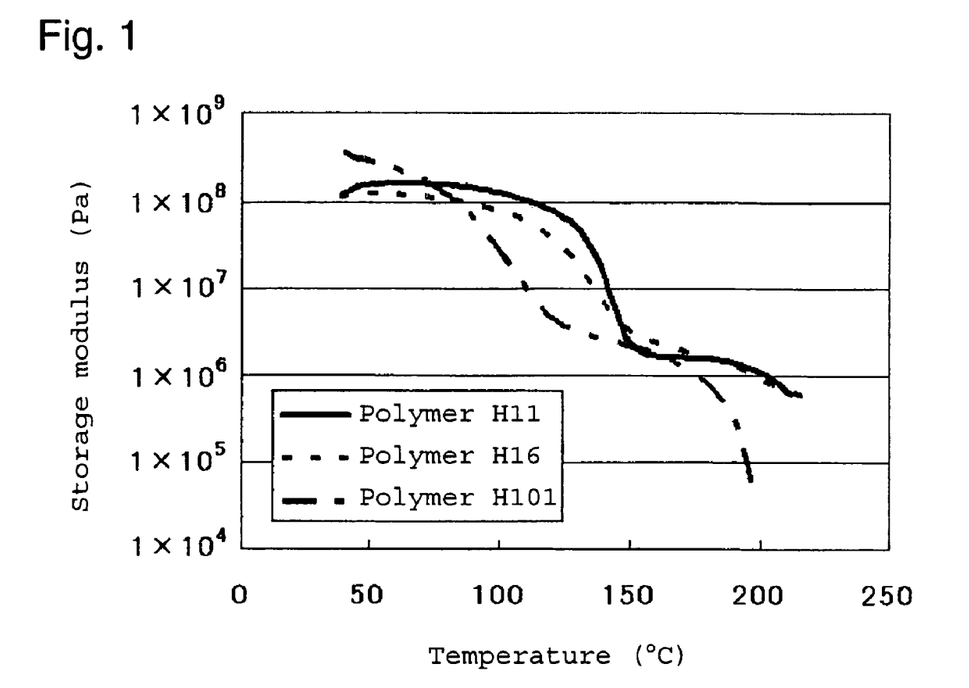
FIG. 1 is a graph showing a relation between the storage modulus and the temperature with respect to polymers of the present invention.

FIG. 1 shows the relation between the temperature and the storage modulus obtained by carrying out a dynamic viscoelasticity measurement by using films of the polymer H11 obtained by copolymerizing TFE and the compound (m11), followed by conversion to an acid-form and the polymer H16 obtained by copolymerizing TFE and the compound (m12), followed by conversion to an acid-form. For the purpose of comparison, that of the polymer H101 obtained by copolymerizing TFE and PSVE, followed by conversion to an acid form, is also shown. It is evident that as compared with the conventional polymer obtained by copolymerizing TFE and PSVE, followed by conversion to is an acid-form, with respect to the polymer obtained by copolymerizing the compound (m11) or (m12) and TFE, followed by conversion to an acid form, the softening temperature and the glass transition temperature are high.

Figure 2:
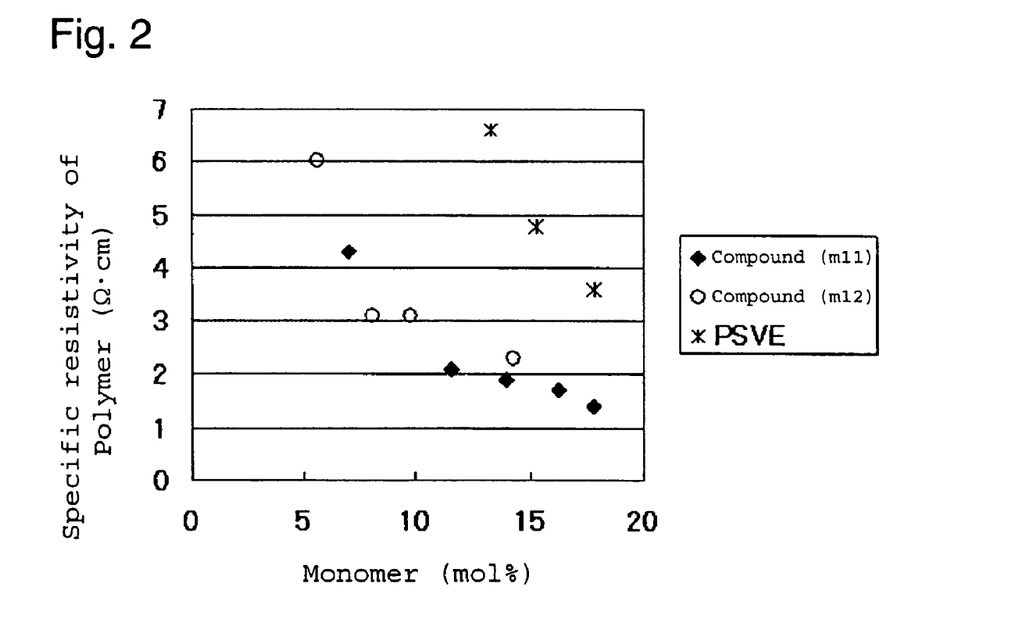
FIG. 2 is a graph showing a relation between the monomer composition and the specific resistivity of its polymer.

FIG. 2 shows the relation between the specific resistivity of an acid-form polymer and the content (mol %) of the compound (m11), the compound (m12) or PSVE in the polymer. It is evident that with the polymer obtained by copolymerizing the compound (m11) or (m12) having two fluorosulfonyl groups, and TFE, followed by conversion to an acid form, the resistance is lower, even if the monomer content is small, than that of the conventional polymer obtained by copolymerizing PSVE and TFE. As the content of the vinyl ether monomer is lower and the TFE content is higher, the mechanical strength becomes higher, and accordingly, it is evident that when the compound (m11) or (m12) is used, it is possible to obtain an acid-form polymer having a low resistance and high strength as compared with a case where PSVE is used.

INDUSTRIAL APPLICABILITY

The present invention provides a compound containing two fluorosulfonyl groups, a compound very useful as an reaction intermediate for the compound, and methods for their production. A polymer obtained by polymerizing the compound, has two sulfonic acid groups in one side chain, whereby the softening temperature is high, and the mechanical strength (such as the elastic modulus in a high temperature range) is excellent. Further, a polymer electrolyte made of the polymer of the present invention has low resistance. Thus, a useful electrolyte material is provided which may be used for an ion exchange membrane (an ion exchange membrane for electrolysis of sodium chloride or an ion exchange membrane for a fuel cell) or for a catalyst layer for a fuel cell.

The entire disclosure of Japanese Patent Application No. 2005-217110 filed on Jul. 27, 2005 including specification, claims, drawings and summary is incorporated herein by reference in its entirety.

What is claimed is:

1. A method for producing a polymer, characterized in that a compound of the following formula (m0) is polymerized to obtain a polymer comprising units based on the compound of the following formula (m0):

(m0)

provided that the symbols in the formula have the following meanings:
$R^{F01}$ is a single bond or a $C_{1-6}$ bivalent perfluoro organic group,
$R^{F02}$ is a $C_{1-6}$ bivalent perfluoro organic group, and
n is 0 or 1.

2. A method for producing a polymer, characterized in that a compound of the following formula (m0) and tetrafluoroethylene are copolymerized to obtain a polymer comprising units based on the compound of the following formula (m0) and units based on tetrafluoroethylene:

(m0)

provided that the symbols in the formula have the following meanings:
$R^{F01}$ is a single bond or a $C_{1-6}$ bivalent perfluoro organic group,
$R^{F02}$ is a $C_{1-6}$ bivalent perfluoro organic group, and
n is 0 or 1.

3. A compound of the following formula (m1):

(m1)

provided that the symbols in the formula have the following meanings:
$R^{F11}$ is a single bond or a $C_{1-6}$ linear perfluoroalkylene group which may have an etheric oxygen atom,
$R^{F12}$ is a $C_{1-6}$ linear perfluoroalkylene group, and
n is 0 or 1.

4. A compound of the following formula (m11):

(m11)

5. A compound of the following formula (m12):

(m12)

6. A compound of the following formula (m13):

(m13)

7. A polymer comprising units based on the compound as defined in claim 3.

8. A polymer comprising units based on the compound as defined in claim 3 and units based on tetrafluoroethylene.

9. A polymer having the —$SO_2F$ groups of the polymer as defined in claim 7 converted to —$SO_3H$ groups.

10. A polymer having the —$SO_2F$ groups of the polymer as defined in claim 8 converted to —$SO_3H$ groups.

11. A polymer comprising units based on the compound of the following formulas (m11), (m12) or (m13):

12. A polymer comprising units based on the compound of the following formulas (m11), (m12) or (m13) and units based on tetrafluoroethylene:

13. A polymer having the —$SO_2F$ groups of the polymer as defined in claim 11 converted to —$SO_3H$ groups.

14. A polymer having the —$SO_2F$ groups of the polymer as defined in claim 12 converted to —$SO_3H$ groups.

* * * * *

UNITED STATES PATENT AND TRADEMARK OFFICE
CERTIFICATE OF CORRECTION

PATENT NO. : 7,531,610 B2  
APPLICATION NO. : 12/010586  
DATED : May 12, 2009  
INVENTOR(S) : Kaneko et al.

Page 1 of 1

It is certified that error appears in the above-identified patent and that said Letters Patent is hereby corrected as shown below:

On the title page, Item (30), The Foreign Application Priority Data has been omitted. Item (30) should read:

Item -- (30)    Foreign Application Priority Data

July 27, 2005   (JP)................................................ 2005-217110 --

Signed and Sealed this

Thirtieth Day of June, 2009

JOHN DOLL  
*Acting Director of the United States Patent and Trademark Office*